US009612229B2

(12) United States Patent
Pretre et al.

(10) Patent No.: US 9,612,229 B2
(45) Date of Patent: Apr. 4, 2017

(54) METHOD AND MEASURING APPARATUS FOR DETERMINING PHYSICAL PROPERTIES OF GAS

(71) Applicant: MEMS AG, Brugg (CH)

(72) Inventors: Philippe Pretre, Dattwil (CH); Andreas Kempe, Zurich (CH); Tobias Suter, Kilchberg (CH)

(73) Assignee: MEMS AG, Brugg (CH)

( * ) Notice: Subject to any disclaimer, the term of this patent is extended or adjusted under 35 U.S.C. 154(b) by 286 days.

(21) Appl. No.: 14/282,562

(22) Filed: May 20, 2014

(65) Prior Publication Data

US 2014/0345363 A1 Nov. 27, 2014

(30) Foreign Application Priority Data

May 24, 2013 (EP) ..................................... 13002708

(51) Int. Cl.
*G01N 33/22* (2006.01)
*G01N 25/36* (2006.01)
(Continued)

(52) U.S. Cl.
CPC ........... *G01N 33/0062* (2013.01); *G01N 7/00* (2013.01); *G01N 25/18* (2013.01); *G01N 25/36* (2013.01); *G01N 33/225* (2013.01)

(58) Field of Classification Search
CPC .. G01N 25/18; G01N 33/0062; G01N 33/225; G01N 7/00
See application file for complete search history.

(56) References Cited

U.S. PATENT DOCUMENTS 4,154,099 A * 5/1979 Blu ...................... G01N 25/005
374/31
4,384,792 A * 5/1983 Sommers ............... G01N 11/08
374/36
(Continued)

FOREIGN PATENT DOCUMENTS

EP 0 591 639 4/1994
EP 1 265 068 12/2002
(Continued)

OTHER PUBLICATIONS

Stamps, Douglas, and Sheldon Tieszen. "Blowout of turbulent jet diffusion flames." Fuel 118 (Feb. 15, 2014): 113-122.*
(Continued)

*Primary Examiner* — Lisa Caputo
*Assistant Examiner* — Punam Roy
(74) *Attorney, Agent, or Firm* — Nixon & Vanderhye P.C.

(57) ABSTRACT

A method for determining physical properties of combustion including: flowing a gas a critical nozzle and past a microthermal sensor wherein the mass flow of the gas through the critical nozzle is the same as the mass flow through the microthermal sensor; measuring the pressure drop in a reservoir of gas flowing to the nozzle; determining a first gas property factor based on the measured pressure drop; determining a second gas property factor based on a flow signal generated by the microthermal sensor; determining a thermal conductivity of the gas using the microthermal sensor; and determining a physical property of the combustion based on a correlation of the first and/or second gas property factors and the thermal conductivity.

16 Claims, 7 Drawing Sheets

(51) Int. Cl.
*G01N 25/18* (2006.01)
*G01N 7/00* (2006.01)
*G01N 33/00* (2006.01)

(56) References Cited

U.S. PATENT DOCUMENTS

| | | | |
|---|---|---|---|
| 5,311,447 A * | 5/1994 | Bonne | G01N 33/225 374/44 |
| 7,104,112 B2 * | 9/2006 | Bonne | G01N 1/24 73/23.24 |
| 7,377,152 B2 | 5/2008 | Brekelmans et al. | |
| 7,536,908 B2 * | 5/2009 | Wang | G01F 1/6845 73/204.15 |
| 7,730,766 B2 * | 6/2010 | Ryser | G01N 33/225 73/24.05 |
| 2003/0046983 A1 * | 3/2003 | Sato | G01N 7/00 73/53.01 |
| 2010/0224834 A1 * | 9/2010 | Peng | G01N 9/36 252/372 |
| 2011/0098936 A1 * | 4/2011 | Bats | G01N 33/225 702/24 |
| 2014/0174152 A1 * | 6/2014 | Gil | G01N 7/00 73/25.01 |

FOREIGN PATENT DOCUMENTS

| | | | |
|---|---|---|---|
| EP | 2015056 | 1/2009 | |
| EP | 2 574 918 | 4/2013 | |
| FR | WO 9902964 A1 * | 1/1999 | G01N 9/266 |
| JP | 10090033 A * | 4/1998 | |
| WO | 2004036209 | 4/2004 | |

OTHER PUBLICATIONS

Huang, Liji. City natural gas metering. INTECH Open Access Publisher, 2012.*

* cited by examiner

US 9,612,229 B2

METHOD AND MEASURING APPARATUS FOR DETERMINING PHYSICAL PROPERTIES OF GAS

RELATED APPLICATION

This application claims, pursuant to 35 U.S.C. §119, the benefit of European patent application 13002708.9 filed on May 24, 2013, the entirety of which application is incorporated by reference.

BACKGROUND OF THE INVENTION

The invention relates to a method and a measuring apparatus for determining physical properties and quantities relevant to combustion of gas and gas mixtures. Physical gas properties mean in particular the density, thermal conductivity, heat capacity and viscosity as well as correlatable quantities relevant to combustion, such as the energy content, calorific value, Wobbe index, methane number and/or air requirement of the gas or gas mixture.

In gas-fuel firing control systems it is important to keep the load in the burner constant even at changing fuel gas qualities. The Wobbe index, formed from the calorific value and the root of the density ratio between air and this gas, is the appropriate index for displaying the interchangeability of gases. An identical Wobbe index will then result in a constant thermal load in the burner.

When regulating (natural) gas motors, knowledge of the calorific value at varying (natural) gas qualities is necessary to achieve an increase of performance or efficiency, while for gas the methane number—by analogy to the octane number for gasoline—is used to assess ignition behaviour (knocking effect or misfiring).

An optimal combustion process requires a correct mixing ratio between fuel gas and air-, known as "air requirement". Soot (flue gas) usually forms if there is too little air, and this may damage fuel cells in particular. Too much air during combustion results in reduced performance. The optimal value depends on the application concerned, but changes again with varying gas qualities.

Correlation methods for calculating quantities relevant to combustion have been described in academic literature, see for example U. Wernekinck, "Gasmessung and Gasabrechnung" (Gas metering and gas billing), Vulkan publishers, 2009, ISBN 978-3-8027-5620-7. The following combinations of measured variables are used in this connection:

A. Dielectric constant, sonic velocity, $CO_2$ content
B. Sonic velocity at 2 pressures, $CO_2$ content
C. Thermal conductivity at 2 temperatures, sonic velocity
D. Thermal conductivity, heat capacity, dynamic viscosity
E. Thermal conductivity, infrared absorption (not dispersive)
F. Infrared absorption (dispersive)

There are currently only a few commercially available devices that are approved for calorific value readings, e.g. the EMC500 device by RMG-Honeywell (Type D plus $CO_2$ content) or the Gas-lab Q1 device by Elster-Instromet (Type E plus $CO_2$ content). However, due to the high acquisition costs, none of these devices is suitable for mass distribution.

Integrated CMOS hot-wire anemometers are able to take a microthermal measurement of thermal conductivity as well as of mass flow. For this technology, reference is made to the publication of D. Matter, B. Kramer, T. Kleiner, B. Sabbattini, T. Suter, "Mikroelektronischer Haushaltsgaszähler mit neuer Technologie" (Micro-electronic household gas meter using new technologies), published in *Technisches Messen* 71, 3 (2004), pp. 137-146. It differs from conventional thermal mass flow meters by taking the measurement directly in the gas flow and not from the outside on a metal capillary tube that encompasses the gas flow.

EP 2 015 056 A1 describes a thermal flow sensor for determining a quantity relevant to combustion, based on a thermal conductivity reading if the mass flow is basically known. A critical nozzle is used to keep the mass flow constant, and the aim is to correct the gas type dependence of the critical nozzle by means of the thermal conductivity. However, the information on the correlation of quantities relevant to combustion is limited to two more or less independent measured variables and thus does not permit validation of the measured data.

WO 2004/036209 A1 describes a sensor for determining a quantity relevant to combustion where the mass flow is kept constant and where a value that is proportional to the heat capacity is identified by means of a thermal measurement. Since the described sensor is not a microthermal sensor, it is not possible to draw conclusions regarding thermal conductivity; this means that the determination of the heat capacity and the quantities relevant to combustion derived therefrom is only possible up to one proportionality factor. As a result, an additional calibration with known gas compositions is required. In addition, the information on thermal conductivity, and thus the means to correlate thermal conductivity $\lambda$ with a quantity relevant to combustion is omitted. Furthermore, the accuracy of this method is limited by the occurring variations of the inaccessible thermal conductivity $\lambda$.

SUMMARY OF THE INVENTION

Hence the invention is based on the objective of presenting a method and a measuring apparatus to determine physical properties of gas and gas mixtures in order to achieve a higher degree of accuracy than the sensors from the above referenced patent documents; in addition, the objective is to produce the measuring apparatus at a lower cost than the devices commercially available that are approved for calorific value readings requiring calibration.

The concept of the invention is to determine physical gas properties, based on measuring the pressure drop of a specified volume of gas through a critical nozzle in combination with a microthermal sensor able to measure the flow as well as thermal conductivity. Both the measurement of the pressure drop and of the flow can be validated for consistency, since the same mass flow for the critical nozzle is also applied to the microthermal sensor.

From these three measured variables it is possible to determine additional values through correlations.

Measuring the Drop in Pressure of a Defined Volume of Gas Using a Critical Nozzle:

The mass flow $\dot{m}$ through a critical nozzle is described by $$\dot{m} = C_d \cdot p \cdot A^* \cdot \psi_{max} \cdot \sqrt{\frac{M}{T \cdot R_m}}, \qquad (1)$$

in which case $C_d$ represents the "discharge coefficient", i.e. the loss factor of an actual critical nozzle compared to an ideal critical nozzle, p the inlet pressure, $A^*$ the nozzle cross-section, T the inlet temperature, $R_m$ the universal gas constant, M the molecular weight of the gas and $\psi_{max}$ the maximum value of the critical flow factor. The latter is a function of the isentropic coefficient $\gamma=c_p/c_V$ (ratio of isobaric to isochoric heat capacity), $$\psi = \sqrt{\gamma} \cdot \left(\frac{\gamma+1}{2}\right)^{\frac{\gamma+1}{2(1-\gamma)}}. \quad (2)$$

If the gas of a known volume V of gas is released from high pressure through the critical nozzle (e.g., from 9 to 4 bar), then according to the ideal gas law, pressure in the volume depends on the time t as follows:

$$p(t) = m(t) \cdot \frac{R_m \cdot T}{M \cdot V}. \quad (3)$$

Therefore, the rate at which the pressure changes results in $$\frac{dp(t)}{dt} = \frac{dm(t)}{dt} \cdot \frac{R_m \cdot T}{M \cdot V} \quad (4)$$
$$= \dot{m}(t) \cdot \frac{R_m \cdot T}{M \cdot V}$$

and together with equation (1) as $$\frac{dp(t)}{dt} = C_d \cdot p \cdot A^* \cdot \psi_{max} \cdot \sqrt{\frac{M}{T \cdot R_m}} \cdot \frac{R_m \cdot T}{M \cdot V} \quad (5)$$
$$= C_d \cdot \frac{A^* \cdot \psi_{max}}{V} \cdot \sqrt{\frac{R_m \cdot T}{M}} \cdot p(t).$$

Accordingly, if the course of the pressure is measured in dependence of the time, then the time constant τ of the related exponential function obtained by integration can be defined as:

$$1/\tau = \frac{C_d \cdot A^* \cdot \psi_{max}}{V} \cdot \sqrt{\frac{R_m \cdot T}{M}}. \quad (6)$$

If the measuring process additionally delivers the value for temperature T, a gas property factor can be defined by omitting all gas-unrelated variables $$\Gamma^* := C_d \cdot \psi_{max} \cdot \sqrt{\frac{1}{M}}. \quad (7)$$

Conversely, if the gas is released from a higher pressure level through the critical nozzle into a known volume V (e.g., from ambient pressure to vacuum), the equation (5') for the pressure increase in volume V reads as follows:

$$\frac{dp(t)}{dt} = C_d \cdot p_{Nozzle} \cdot A^* \cdot \psi_{max} \cdot \sqrt{\frac{M}{T \cdot R_m}} \cdot \frac{R_m \cdot T}{M \cdot V} \quad (5')$$

$$= C_d \cdot \frac{A^* \cdot \psi_{max}}{V} \cdot \sqrt{\frac{R_m \cdot T}{M}} \cdot p_{Nozzle},$$

in which case the pressure before the nozzle $p_{nozzle}$ remains constant, which leads over time to a linear pressure increase in volume V with $$\frac{C_d \cdot A^* \cdot \psi_{max}}{V} \cdot \sqrt{\frac{R_m \cdot T}{M}} \cdot p_{Nozzle} \quad (6')$$

being a proportionality constant. If, in addition, the values of the temperature T and the nozzle inlet pressure $p_{Nozzle}$ are obtained by the measurement, it is possible to define in turn the gas property factor $$\Gamma^* := C_d \cdot \psi_{max} \cdot \sqrt{\frac{1}{M}} \quad (7')$$

by omitting all gas-unrelated variables.

Mass Flow Measurement by Means of a Microthermal Sensor:

The starting point for describing the microthermal mass flow measurement is that of the one-dimensional thermal conductivity equation describing the microthermal system (Kerson Huang: *Statistical Mechanics*, 2nd volume, John Wiley & Sons, New York 1987, ISBN 0-471-85913-3):

$$\frac{c_p}{\lambda} \cdot \rho v_x \cdot \frac{d}{dx}T = \nabla^2 T + \frac{1}{\lambda}\Theta, \quad (8)$$

in which
  $v_x$ represents the component of the mean flow rate (velocity vector) $\vec{v}$ in the direction of x, i.e. in the direction of the gas flow,
  T represents temperature, $$\frac{d}{dx}T$$

represents the temperature gradient,
  $c_p$ represents the heat capacity of the gas at constant pressure,
  ρ represents density,
  λ represents the thermal conductivity of the gas,
  $\nabla^2 T$ represents the Laplacian operator, applied to temperature T, in which $$\nabla^2 = \left(\frac{d}{d_x}\right)^2 + \left(\frac{d}{dy}\right)^2 + \left(\frac{d}{dz}\right)^2.$$

Since the gas (gas flow) flows only in the direction x, the components $v_y$ and $v_z$ in direction y, respectively direction z of the mean flow rate $\vec{v}$ are taken to be zero. Θ with the unit Watt/m³ describes the source term of the heat element. In the microthermal method, the source term is the heating wire of a miniaturised, integrated hot-wire anemometer, which feeds thermal energy into the system. From the solution of equation (8), which describes the temperature distribution in the microthermal system, it is possible, by measuring this temperature distribution, to determine the factor S, $$S := \frac{c_p}{\lambda} \cdot \rho \cdot v_x = \frac{c_p}{\lambda} \cdot \frac{\dot{m}}{A}, \qquad (9)$$

wherein A means the cross-section of the flow channel past the microthermal sensor. In combination with the critical nozzle, i.e. by arranging the microthermal sensor after the critical nozzle, the mass flow is provided by equation (1), therefore by $$\frac{c_p}{\lambda} \cdot \rho \cdot v_x = \frac{c_p}{\lambda} \cdot C_d \cdot p \cdot \frac{A^*}{A} \cdot \psi_{max} \cdot \sqrt{\frac{M}{T \cdot R_m}}. \qquad (10)$$

Measuring pressure p and temperature T, and omitting again all gas-unrelated variables, delivers a second gas property factor $$\Gamma = \frac{c_p}{\lambda} \cdot C_d \cdot \psi_{max} \cdot \sqrt{M}. \qquad (11)$$

The omission of all gas-unrelated variables in equation (7) and equation (11) is done implicitly, by putting $\Gamma$ and $\Gamma^*$ in relation to $\Gamma$ and $\Gamma^*$ of a known (calibration) gas. See also FIG. 4.

Measuring Thermal Conductivity by Means of Microthermal Sensor:

It should be noted that the thermal conductivity $\lambda$, due to the source term $\Theta$, has an additional, separate impact on the solution of equation (8). The same applies in reverse: the thermal conductivity can be determined if the microthermal sensor is measured without an applied mass flow ($v_x=0$ or $\dot{m}=0$). The related differential equation for temperature distribution then simply reads $$\nabla^2 T = -\frac{1}{\lambda}\Theta. \qquad (12)$$

Validation of the Gas Property Factors $\Gamma$ or $\Gamma^*$:

The ratio of the two gas property factors $\Gamma$ and $\Gamma^*$ results in $$\Gamma/\Gamma^* = \frac{c_p}{\lambda} \cdot M \propto \frac{c_p}{\lambda} \cdot \rho_{norm}, \qquad (13)$$

since the molecular weight is proportional to the standard density (density at standard conditions 1013.25 mbar and 273.15 K), due to the fact that for most gases, the mol volume is almost identical. Thus, in equation (9), the flow rate $v_x$ and, in conjunction with the flow channel cross-section A, the standard volume flow $\phi_{norm}=v_x \cdot A$ can be extracted from the factor S, measured with the microthermal sensor. The integration of this volume flow over time, i.e. the time interval $t_2-t_1$, should then correspond with the released gas volume calculated on the basis of the corresponding pressure and temperature values:

$$\int_{t_1}^{t_2} \phi_{norm}(t)\, dt \stackrel{!}{=} \frac{(p(t_2)-p(t_1))}{1013.25 \text{ mbar}} \cdot \frac{273.15 \text{ K}}{T} \cdot V. \qquad (14)$$

If these two values do not match, the standard volume flow or the pressure signal can be adjusted, depending on which value can be measured less accurately, to the point that equation (14) is satisfied. In the case of a standard volume flow adjustment for $v_x=\phi_{norm}/A$, the right side of the equation (13) is also adjusted through the measured factor S in equation (9), and thus also the gas property factor $\Gamma$, again by aid of equation (13). In the case of a pressure signal adjustment, the time constant $\tau$ in equation (6), respectively the proportionality constant in equation (6'), is adjusted, which in turn leads to an adjustment of the gas property factor $\Gamma^*$ in equation (7) or (7'). In this way, $\Gamma$ and $\Gamma^*$ have been defined consistently, because the mass flow through the nozzle is the same as the mass flow with which the microthermal sensor is supplied.

Correlation of Quantities Relevant to Combustion:

By measuring the gas property factors $\Gamma$ and $\Gamma^*$ as well as thermal conductivity $\lambda$, three independent measured variables are obtained, with which it is now possible to correlate quantities relevant to combustion Q by aid of a function $f_{corr}$:

$$Q_{corr}=f_{corr}(\Gamma,\Gamma^*,\lambda). \qquad (15)$$

For example, for correlating the density ratio $\rho_{corr}/\rho_{ref}$ at 0° C. and 1013.25 mbar, as shown in FIG. 4, the following correlation function $$\rho_{corr}/\rho_{ref}=f_{corr}(\Gamma,\Gamma^*,\lambda)=\Gamma^r \cdot \Gamma^{*s} \cdot \lambda^t \qquad (15)$$

is obtained, with exponents r=−0.2, s=−1.8 and t=−0.2 and a typical H-gas used for reference purposes.

Method and Measuring Apparatus According to the Present Invention

In the method for determining physical properties and/or quantities relevant to combustion of gas and gas mixtures according to the present invention:

the gas or gas mixture flows from a gas reservoir through a critical nozzle and past a microthermal sensor, with the same mass flow being applied to the critical nozzle and the microthermal sensor;

the pressure drop in the gas reservoir is measured as a function of time;

a first gas property factor $\Gamma^*$, dependent on a first group of physical properties of the gas or gas mixture, is determined on the basis of the measured values of the pressure drop, with the first gas property factor being derived, for example, from a time constant of the pressure drop;

a second gas property factor $\Gamma$, dependent on a second group of physical properties of the gas or gas mixture, is determined by the flow signal of the microthermal sensor, with the second gas property factor containing, for example, the heat capacity $c_p$ of the gas or gas mixture, or being dependent on the same;

the thermal conductivity $\lambda$ of the gas or gas mixture is determined with the aid of the microthermal sensor; and a desired physical property or quantity relevant to combustion is determined by the first and/or second gas property factor $\Gamma^*$, $\Gamma$ and thermal conductivity $\lambda$ through correlation.

The method is advantageously based on an exponential decline of the measured pressure and derives the first gas property factor $\Gamma^*$ from the time constant of the pressure drop, in which case the first gas property factor is formed, for example, by measuring additionally temperature T and by omitting all gas-unrelated variables.

The second gas property factor ($\Gamma$) typically contains the quotient of the heat capacity $c_p$, divided by the thermal conductivity $\lambda$ of the gas or gas mixture, or is dependent on the same, with the second gas property factor being formed by measuring in addition, for example, the temperature T and by omitting all gas-unrelated variables.

According to an advantageous embodiment of the method, the gas property factors $\Gamma^*$, $\Gamma$ are validated by comparing the values for the total volume of the released gas or gas mixture; this is done by measuring the pressure and temperature in the gas reservoir at the start and the end of the pressure drop reading and by determining the released standard volume at a known volume of the gas reservoir, by accumulating the standard flow measured with the microthermal sensor across the time interval between the start and end of the pressure drop reading, and by comparing the released standard volume to the accumulated standard flow. In case of a discrepancy, the first and/or the second gas property factor is adjusted, e.g. by adjusting the pressure signal or the standard flow value of the microthermal sensor.

The embodiment of the method described above can be used to calibrate the flow signal of the microthermal sensor by calibrating the flow signal of the microthermal sensor for a specific calibration gas or gas mixture, by determining the ratio $\Gamma/\Gamma^*$ of the second gas property factor, derived from the flow signal of the microthermal sensor, to the first gas property factor for an unknown gas or gas mixture, and by comparing the standard volume values from the pressure drop reading and the accumulated standard flow of the microthermal sensor, and to use them to adjust the ratio of the second gas property factor to the first and to adapt the value for the second gas property factor $\Gamma$.

In a further advantageous embodiment of the method for determining physical properties and/or quantities relevant to combustion of the gas or gas mixture:

- the gas or gas mixture flows under pressure through a critical nozzle and past a microthermal sensor into a gas reservoir, with the same mass flow being applied to the critical nozzle and the microthermal sensor;
- the pressure increase in the gas reservoir is measured as a function of time;
- a first gas property factor $\Gamma^*$, dependent on a first group of physical properties of the gas or gas mixture, is determined by reference to the measured variables of the pressure increase;
- a second gas property factor $\Gamma$, dependent on a second group of physical properties of the gas or gas mixture, is determined from the flow signal of the microthermal sensor, with the second gas property factor containing, for example, the heat capacity $c_p$ of the gas or gas mixture, or being dependent on the same;
- the thermal conductivity $\lambda$ of the gas or gas mixture is determined with the aid of the microthermal sensor; and
- a desired physical property or quantity relevant to combustion is determined from the first and/or second gas property factor $\Gamma^*$, $\Gamma$ and thermal conductivity $\lambda$ through correlation.

The method is advantageously based on a linear increase of the measured pressure and derives the first gas property factor $\Gamma^*$ from the proportionality constant of the pressure increase, in which case the first gas property factor is formed, for example, by measuring additionally the temperature T and the nozzle inlet pressure $p_{Nozzle}$ and by omitting all gas-unrelated variables.

The second gas property factor $\Gamma$ typically contains the quotient of the heat capacity $c_p$ divided by the thermal conductivity $\lambda$ of the gas or gas mixture or is dependent on the same, in which case the second gas property factor is formed, for example, by measuring additionally the temperature T and by omitting all gas-unrelated variables.

According to a further advantageous embodiment of the method, the gas property factors $\Gamma^*$, $\Gamma$ are validated by comparing the values for the total volume of the gas or gas mixture flown into the gas reservoir; this is done by measuring the pressure and temperature in the gas reservoir at the start and end of the pressure increase reading and by determining the standard volume fed into the gas reservoir at a known volume of the gas reservoir, by accumulating the standard flow measured with the microthermal sensor across the time interval between the start and end of the pressure increase reading, and by comparing the standard volume fed into the gas reservoir to the accumulated standard flow. In case of a discrepancy, the first and/or the second gas property factor is adjusted, e.g. by adjusting the pressure signal or the standard flow value of the microthermal sensor.

The embodiment of the method described above can be used to calibrate the flow signal of the microthermal sensor by calibrating the flow signal of the microthermal sensor for a specific calibration gas or gas mixture, by determining the ratio $\Gamma/\Gamma^*$ of the second gas property factor, derived from the flow signal of the microthermal sensor, to the first gas property factor for an unknown gas or gas mixture, and by comparing the standard volume values from the pressure increase reading and the accumulated standard flow of the microthermal sensor, and to use them to adjust the ratio of the second gas property factor to the first and to adapt the value for the second gas property factor $\Gamma$.

The desired physical property may be, for example, the density or the thermal conductivity or the heat capacity or the viscosity of the gas or gas mixture, and the quantity relevant to combustion may be, for example, the energy content or the calorific value or the Wobbe index or the methane number or the air requirement of the gas or gas mixture.

The desired physical property or quantity relevant to combustion Q is determined advantageously by aid of a correlation function $Q=f_{corr}(\Gamma, \Gamma^*, \lambda)=\text{const}\cdot\Gamma^r\cdot\Gamma^{*s}\cdot\lambda^t$, wherein r, s and t are exponents, and const is a constant.

The pressure in the gas reservoir at the start of the pressure drop measurement is typically higher than the critical pressure $p_{crit}$ of the critical nozzle and the external pressure downstream of the critical nozzle is less than half the critical pressure, or the pressure in the gas reservoir at the start of the pressure increase reading is typically less than half the critical pressure $p_{crit}$ of the critical nozzle and the pressure upstream of the critical nozzle is higher than the critical pressure.

The gas reservoir is typically disconnected from the gas supply during the measurement, irrespective of the embodiment and variant. The volume of the gas reservoir can be selected advantageously in such a way that the pressure inside the gas reservoir significantly decreases or increases by the end of the measurement, for example, by at least a tenth or a fifth of the initial pressure.

The measuring apparatus for determining physical properties and/or quantities relevant to combustion of a gas or gas mixture according to the present invention includes an analyzer unit that is configured to carry out a procedure in accordance with one of the embodiments or variants described above, as well as a gas reservoir, that is equipped with a pressure sensor, a critical nozzle and a microthermal sensor to measure the flow and thermal conductivity. In this set-up the gas reservoir is connected to the critical nozzle and the microthermal sensor for the purposes of measuring.

Furthermore, the invention also includes the use of a gas reservoir and a critical nozzle to determine physical properties and/or quantities relevant to combustion of a gas or gas mixture; in this set-up the gas or gas mixture flows under pressure from the gas reservoir through the critical nozzle, and the pressure drop in the gas reservoir is measured as a function of time, a gas property factor $\Gamma^*$, dependant on the physical properties of the gas or gas mixture is determined on the basis of the measured values of the pressure drop, derived, for example, from a time constant of the pressure drop; the gas property factor $\Gamma^*$ then serves to determine a desired physical property or quantity relevant to combustion through correlation.

In another advantageous embodiment, low pressure is generated in the reservoir, and the gas or gas mixture flows under pressure through the critical into the gas reservoir; in this set-up, the pressure increase in the gas reservoir is measured as a function of time, and a gas property factor $\Gamma^*$, dependent on the physical properties of the gas or gas mixture, is determined from the measured values of the pressure increase, which then serves to determine a desired physical property or quantities relevant to combustion through correlation.

The above-described use of a gas reservoir and a critical nozzle to determine physical properties and/or quantities relevant to combustion of a gas or gas mixture, or the corresponding method in which a gas reservoir and a critical nozzle are used for determining physical properties and/or quantities relevant to combustion of a gas or gas mixture, can also be seen as a distinct, independent invention, which may additionally include a measuring apparatus with an analyzer unit, a gas reservoir and a critical nozzle, in which case the analyzer unit is configured for the use of the gas reservoir and the critical nozzle to determine physical properties and/or quantities relevant to combustion of a gas or gas mixture or to carry out the corresponding method.

In addition, the invention encompasses the use of a gas reservoir and a microthermal sensor calibrated for a specific calibration gas or gas mixtures to determine physical properties and/or quantities relevant to combustion of gas or gas mixtures; in this set-up the gas or gas mixture flows under pressure from the gas reservoir past the microthermal sensor, in which case the volume flow $v_x \cdot A$, determined by the microthermal sensor calibrated for a specific calibration gas or gas mixture, is accumulated and compared to the gas volume released from the gas reservoir; from the comparison of the two volumes a gas property factor $S/v'_x$, dependent on the physical properties of the gas or gas mixture, is determined, in which $v'_x$ represents the flow rate of the released gas volume, and in which the desired physical property or quantity relevant to combustion is determined from the gas property factor, which may consist, for example, of $S/v'_x = c_p \cdot \rho/\lambda$ (see equation (9)), through correlation.

In another advantageous embodiment, low pressure is generated in the gas reservoir, and the gas or gas mixtures flows under pressure past the microthermal sensor into the gas reservoir, in which case the volume flow $v_x \cdot A$, determined by the microthermal sensor calibrated for a specific calibration gas or gas mixture, is accumulated and compared to the gas volume flowing into the gas reservoir; from the comparison of the two volumes a gas property factor $S/v'_x$, dependent on the physical properties of the gas or gas mixture, is determined, and in which the desired physical property or quantity relevant to combustion is determined from the gas property factor, which may be represented, for example, by $S/v'_x = c_p \cdot \rho/\lambda$ (see equation (9)), through correlation.

In another advantageous variant of the embodiment, the gas flow is generated by moving a piston.

The above-described use of a gas reservoir and a microthermal sensor calibrated for a specific calibration gas or gas mixture to determine physical properties and/or quantities relevant to combustion of a gas or gas mixture, or the corresponding method, in which a gas reservoir and a microthermal sensor calibrated for a specific calibration gas or gas mixture are used to determine physical properties and/or quantities relevant to combustion of gas or a gas mixture, can also be seen as a distinct, independent invention, which may additionally comprise a measuring apparatus with an analyzer unit, a gas reservoir and a microthermal sensor, in which case the analyzer unit is configured for the use of the gas reservoir and the microthermal sensor to determine physical properties and/or quantities relevant to combustion of a gas or gas mixture or to carry out the corresponding method.

The advantage of the method and measuring apparatus to determine physical properties and/or quantities relevant to combustion of a gas or gas mixture pursuant to the present invention is that three independent measured variables are available for correlating quantities relevant to combustion. This makes it possible, on the one hand, to achieve a comparatively high level of accuracy for determining quantities relevant to combustion, which otherwise can only be achieved with substantially more expensive devices; on the other hand, it is possible to validate the readings and to adjust any deviations.

Other advantages are apparent from the following specification.

SUMMARY OF THE DRAWINGS

The invention is explained in more detail below with reference to the drawings. In the drawings.

DETAILED DESCRIPTION OF THE INVENTION

Figure 1A:
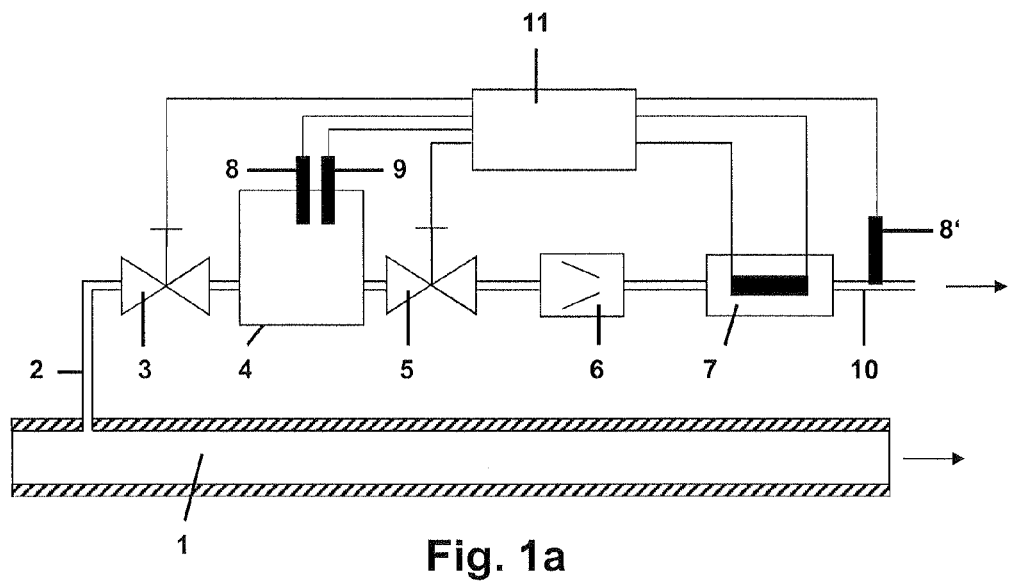
FIG. 1a shows an exemplary embodiment of a schematic configuration of a measuring apparatus according to the present invention (high-pressure variant)

FIG. 1*a* shows an exemplary embodiment of a schematic configuration of a measuring apparatus according to the present invention in which the pressure in the main gas duct 1 is higher than the critical pressure for the critical nozzle 6 of the measuring apparatus (high-pressure variation). In the exemplary embodiment, the measuring apparatus consists, in addition to the critical nozzle 6, of an analyzer unit 11, which is configured for performing the method according to the present invention, a gas reservoir 4, which is equipped with a pressure sensor 8 and a microthermal sensor 7 to measure the flow and thermal conductivity, in which case the gas reservoir 4 is connected with the critical nozzle 6 and the microthermal sensor 7 for the measurements.

If required, the measuring apparatus may comprise one or more of the following additional components: a test line 2, which leads to the gas reservoir 4, and which may be connected to a main gas duct 1 during operation, an inlet valve 3, which may be arranged in the test line 2 to control the gas supply to the gas reservoir, an outlet valve 5, installed on the outlet side of the gas reservoir to control the flow of gas from the gas reservoir, an outlet 10 for discharging the gas released from the measuring apparatus, an additional pressure sensor 8', which may be installed on the outlet 10, a temperature sensor 9, which is installed in the gas reservoir, and a compressor 12', which may be installed on the inlet side of the gas reservoir 4 to increase the pressure in the gas reservoir.

An exemplary embodiment of the method for determining physical properties and/or quantities relevant to combustion of gas or gas mixtures according to the present invention is described below with reference to FIG. 1*a*. In this method, the gas or gas mixture flows from a gas reservoir 4 through a critical nozzle 6 and past a microthermal sensor 7, with the same mass flow being applied to the critical nozzle and the microthermal sensor. The pressure drop in gas reservoir 4 is measured as a function of time and a first gas property factor $\Gamma^*$, dependent on a first group of physical properties of the gas or gas mixture, is determined on the basis of the measured values of the pressure drop, with the first gas property factor being derived, for example, from a time constant of the pressure drop. A second gas property factor $\Gamma$, dependent on a second group of physical properties of the gas or gas mixture, is calculated from the flow signal of the microthermal sensor 7, with the second gas property factor including, for example, the heat capacity $c_p$ of the gas or gas mixture, or being dependent on the same. Next, the thermal conductivity $\lambda$ of the gas or gas mixture is determined with the aid of the microthermal sensor 7, and the desired physical property or quantity relevant to combustion is determined by aid of correlation on the basis of the first and/or second gas property factor $\Gamma^*$, $\Gamma$ and the thermal conductivity.

Other advantageous embodiments and variants of the method are described in the preceding sections of the specification. The following description provides additional details on the method that may be used if desired.

Advantageously, the inlet valve 3 and the outlet valve 5 are opened first to allow the gas or gas mixture that is to be measured to flow from the main gas duct 1 through the test line 2 and through the measuring apparatus to ensure that no extraneous gas from a previous measurement remains in the measuring apparatus. The inlet valve and outlet valve can be opened via a control unit. In individual cases, the analyzer unit 11, too, can control the inlet valve and the outlet valve, as shown in FIG. 1*a*. In this case, the outlet valve 5 closes and the gas reservoir 4, the volume content V of which is known, fills up until the inlet valve 3 is closed. Pressure p and temperature T in the gas reservoir can be measured with the pressure sensor 8 or the temperature sensor 9, to ensure that the standard volume $V_{norm}$ of the gas or gas mixture contained in the gas reservoir can be deduced at any time.

$$V_{norm} = \frac{p}{1013.25 \text{ mbar}} \cdot \frac{273.15 \text{ K}}{T} \cdot V. \tag{17}$$

If the pressure p in the gas reservoir 4 is higher than the pressure $p_{crit}$, which is required to critically operate nozzle 6, the outlet valve 5 can be opened again. By preference, the pressure p in the gas reservoir exceeds $p_{crit}$ by several bars, so that the pressure drop reading can be performed during this phase of overpressure, while nozzle 6 is always operated critically. Outlet valve 5 now closes again, which concludes the pressure drop measurement. By preference, pressure sensor 8 is installed as a differential pressure sensor relative to the outlet 10 of the measuring apparatus. However, it is also possible to provide an additional pressure sensor 8' at the outlet.

During the pressure drop reading, the time-dependent pressure p(t) and the time-dependent temperature T(t) in the pressure reservoir 4 has been measured and recorded by the analyzer unit 11. With these data, the time constant $\tau$ in equation (6) or the gas property factor $\Gamma^*$ in equation (7) is determined in the analyzer unit. At the same time, flow data have been measured with the microthermal sensor 7, which were recorded in turn by the analyzer unit to determine the factor S in equation (9) or the gas property factor $\Gamma$ in equation (11). Since the inlet valve and the outlet valve close after the pressure drop reading, no gas flows past the microthermal sensor 7 anymore. Now the measurement of the thermal conductivity reading $\lambda$, can take place. The thermal conductivity $\lambda$, recorded in turn by the analyzer unit, is determined with the aid of equation (12).

Now the (optional) validation of the gas property factor $\Gamma$ or $\Gamma^*$ respectively takes place in the analyzer unit 11. Thereafter, depending on the desired quantity relevant to combustion Q, the calculation of this value by aid of equation (15) with the previously determined correlation function $Q_{corr}=f_{corr}(\Gamma, \Gamma^*, \lambda)$ is made.

Figure 1B:
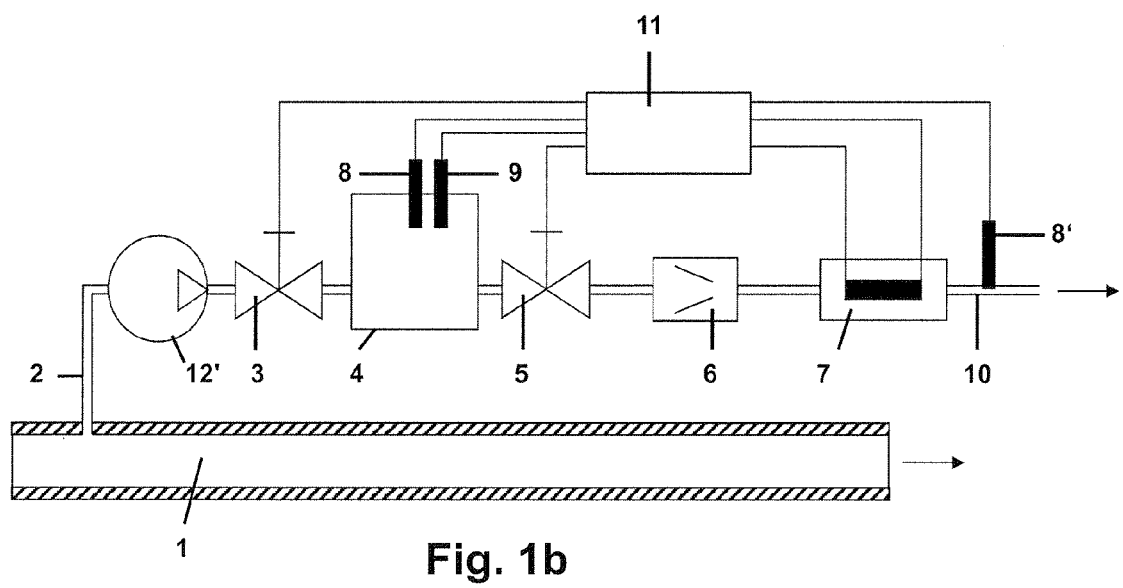
FIG. 1b shows a variant of the exemplary embodiment shown in FIG. 1a, FIG. 2 shows a second exemplary embodiment of the schematic configuration of a measuring apparatus according to the present invention (low pressure variant)

If required, it is possible to provide additionally, as shown in FIG. 1b, a compressor 12', installed, for example, on the inlet side of the gas reservoir 4 to increase the pressure in the gas reservoir.

Figure 2:
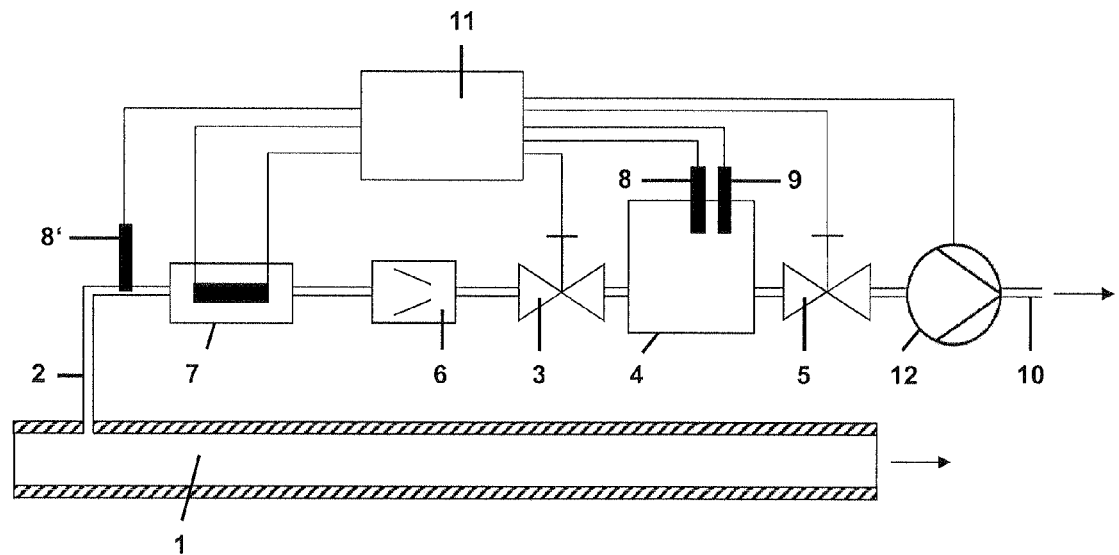

FIG. 2 shows a second exemplary embodiment of the schematic configuration of a measuring apparatus according to the present invention, which is based on low pressure in the gas reservoir. This so-called low pressure variant is advantageous, for example, for the gas supply to end customers. In the second exemplary embodiment, the measuring apparatus comprises, in addition to the gas reservoir 4, a pressure sensor 8 on the gas reservoir, an analyzer unit 11, which is configured to perform a method according to the present invention, a critical nozzle 6 and a microthermal sensor 7 to measure the flow and the thermal conductivity, in which case the gas reservoir 4 is connected with the critical nozzle 6 and the microthermal sensor 7 for the measurement.

If required, the measuring apparatus may comprise one or more of the following additional components: a vacuum pump 12 connected to the gas reservoir 4 to generate low pressure in the gas reservoir, a test line 2 leading to the gas reservoir 4 and which may be connected with a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be located in the test line 2 or main gas duct, and a temperature sensor 9, which is installed in the gas reservoir 4.

An exemplary embodiment of the method for determining physical properties and/or quantities relevant to combustion of gas or gas mixtures according to the present invention is described below with reference to FIG. 2. In this method, the gas or gas mixture flows under pressure through the critical nozzle 6 and past the microthermal sensor 7 into the gas reservoir 4, with the same mass flow being applied to the critical nozzle and the microthermal sensor. The pressure increase in the gas reservoir 4 is measured as a function of time, and a first gas property factor $\Gamma^*$, dependent on a first group of physical properties of the gas or gas mixture, is determined by reference to the measured values of the pressure increase, with the first gas property factor being derived, for example, from a proportionality constant of the pressure increase. A second gas property factor $\Gamma$, dependent on a second group of physical properties of the gas or gas mixture, is calculated from the flow signal of the microthermal sensor 7, with the second gas property factor including, for example, the heat capacity $c_p$ of the gas or gas mixture, or being dependent on the same; Next, the thermal conductivity $\lambda$ of the gas or gas mixture is determined with the aid of the microthermal sensor 7, and the desired physical property or quantity relevant to combustion is determined by aid of correlation on the basis of the first and/or second gas property factor $\Gamma^*$, $\Gamma$ and the thermal conductivity.

Other advantageous embodiments and variants of the method are described in the preceding sections of the specification. The following description provides additional details on the method that may be used if desired.

In a first step, the pressure in gas reservoir 4 is advantageously decreased to such an extent, for example with a vacuum pump 12, that the critical nozzle 6 can be critically operated; in other words, until the pressure in the gas reservoir is less than half the pressure upstream of the critical nozzle. No high vacuum is required. As long as the pressure p and the temperature T can be measured in the gas reservoir 4, it is possible to calculate the gas standard volume that has flown into the gas reservoir. However, it is an advantage if the pressure is by some factor less than required for critical conditions, because this means that the measurement can consume more time accordingly, which makes it possible to determine the proportionality constant more accurately.

For further details on the methods, which may be used if necessary, reference is made to the specification of the first exemplary embodiment, subject to replacement of the term "pressure drop" by the term "pressure increase", where appropriate.

Figure 3:
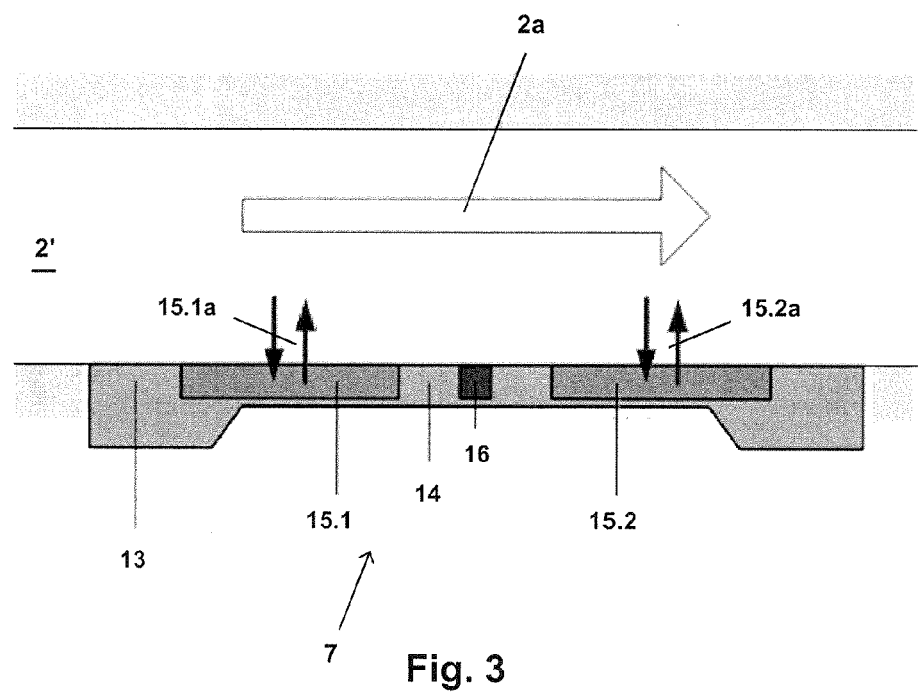
FIG. 3 shows an exemplary embodiment of a microthermal sensor for use in a measuring apparatus according to the present invention.

FIG. 3 shows an exemplary embodiment of a microthermal sensor for use in a measuring apparatus according to the present invention. For example, the microthermal sensor 7 may be—as shown in FIG. 3—an integrated microthermal CMOS hot-wire anemometer that is installed in a section 2' of the test line during normal operation and that can be supplied with a gas or gas mix flow 2a. The microthermal CMOS hot-wire anemometer comprises a substrate 13, which typically contains a membrane 14, which measures only a few micrometers in thickness. Furthermore, the CMOS hot wire anemometer consists of two thermal elements 15.1 and 15.2 and a heating element 16, which can be placed between the two thermo-elements in the direction of the flow. The two thermo-elements 15.1, 15.2 serve to record the resulting temperature generated due to the heat exchange 15.1a, 15.2a in combination with the gas or gas mixture flow 2a.

For further details on the functioning of the CMOS hot wire anemometer, reference is made to D. Matter, B. Kramer, T. Kleiner, T. Suter, "Mikroelektronischer Haushaltsgaszähler mit neuer Technologie" (Micro-electronic domestic gas meters using new technologies), in *Technisches Messen* 71, 3 (2004), pp. 137-146.

Figure 4:
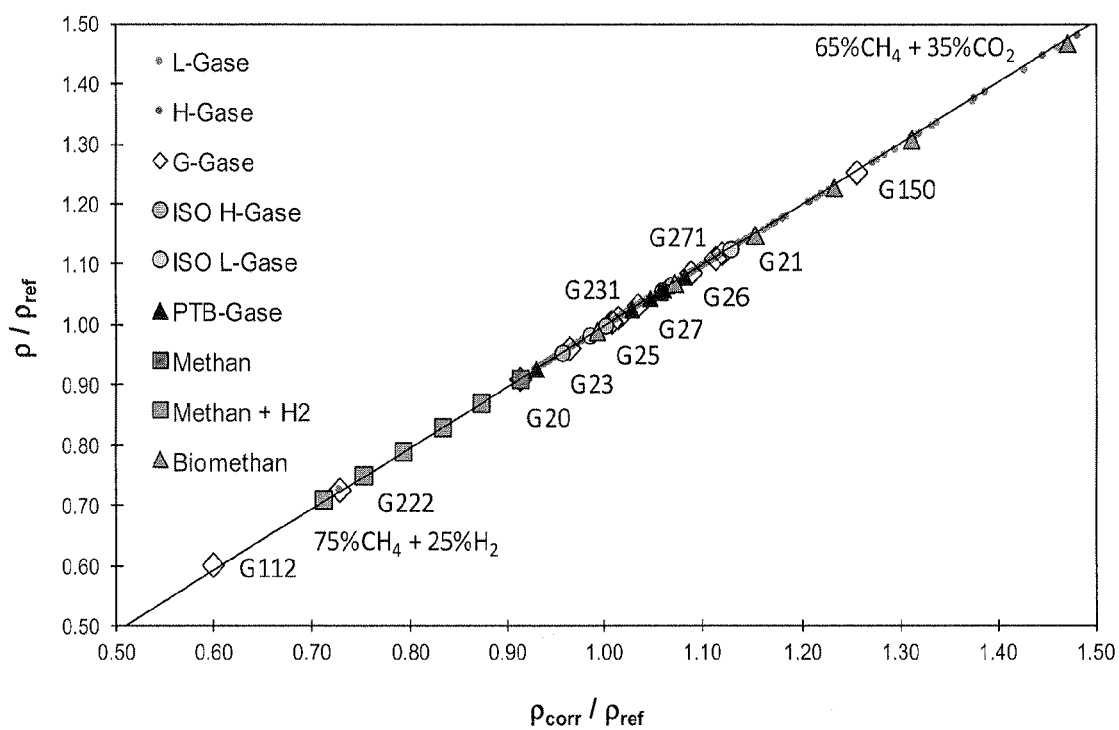
FIG. 4 shows a graphical illustration of the directly measured density ratio (ordinate) as a function of the correlated density ratio (abscissa) for various gas groups at standard conditions (0° C., 1013.25 mbar).

FIG. 4 illustrates the directly measured density ratio $\rho/\rho_{ref}$ (ordinate) as a function of the correlated density ratio $\rho_{corr}/\rho_{ref}$ (abscissa) for various gas groups at standard conditions (0° C., 1013.25 mbar), in which case the correlated density ratio was determined with a method or a measuring apparatus in accordance with the present invention. A typical H-gas was used as a reference gas.

The measuring apparatus described above for determining physical properties and/or quantities relevant to combustion of a gas or gas mixture belongs to a new category, namely "Measurement of the pressure drop or pressure increase in a gas reservoir, wherein the gas flows through a critical nozzle, as well as measurement of thermal conductivity and of flow with the aid of a microthermal sensor, and data validation by summation of the flow values". The components used are inexpensive, which makes it possible to develop new markets, where currently no gas quality sensors are being used for cost reasons. From an accuracy perspective, only a few limitations compared to more expensive, commercially available devices are to be expected, since in this case, too, at least three independent measured variables are being used for the correlation.

Furthermore, the invention comprises in a second embodiment the use of a gas reservoir and a critical nozzle for determining physical properties and/or quantities relevant to combustion of a gas or gas mixture, or a method in which a gas reservoir and a critical nozzle for determining physical properties and/or quantities relevant to combustion of a gas or gas mixture are used, wherein the gas or gas mixture flows under pressure from the gas reservoir through the critical nozzle; in this case, the pressure drop in the reservoir is measured as a function of time, a gas property factor Γ*, dependent on the physical properties of the gas or gas mixture, which is derived, for example, from a time constant of the pressure drop, is determined on the basis of the measured variables of the pressure drop, and a desired physical property or quantity relevant to combustion is determined from the gas property factor Γ* through correlation.

The second embodiment of the invention described above can also be seen as a distinct, independent invention.

Figure 5A:
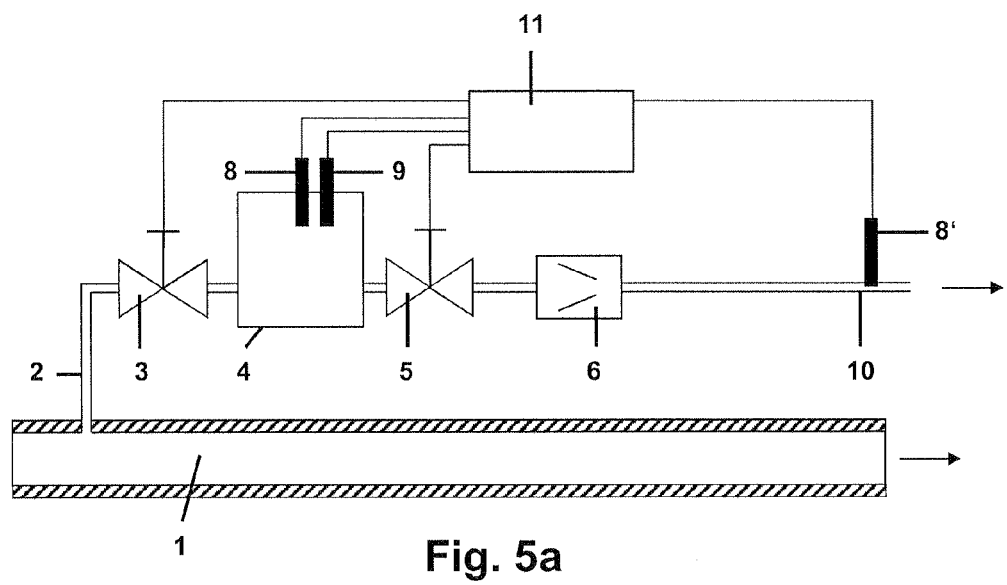
FIG. 5a shows an exemplary embodiment of a schematic configuration of a measuring apparatus according to a second embodiment of the invention (high-pressure variant)

FIG. 5a shows an exemplary embodiment of a schematic configuration of a measuring apparatus according to the second embodiment of the present invention in which the pressure in the main gas duct 1 is higher than the critical pressure for the critical nozzle 6 of the measuring apparatus (high-pressure variation). In the exemplary embodiment the measuring apparatus, in addition to the critical nozzle 6, consists of an analyzer unit 11, which is configured for carrying out a method according to the second embodiment of the invention, and a gas reservoir 4, which is equipped with a pressure sensor 8, in which case the gas reservoir 4 is connected to the critical nozzle 6 for measurement purposes.

If required, the measuring apparatus may comprise one or more of the following additional components: a test line 2, which leads to the gas reservoir 4, and which may be connected to a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be installed on the outlet 10, a temperature sensor 9, which is installed in the gas reservoir, and a compressor 12', which may be located on the inlet side of the gas reservoir 4 to increase the pressure in the gas reservoir.

An exemplary embodiment of the method for determining physical properties and/or quantities relevant to combustion of gas or gas mixtures according to the second embodiment of the invention is described below with reference to FIG. 5a. In this exemplary embodiment, the gas or gas mixture flows from the gas reservoir 4 through the critical nozzle 6. The pressure drop in gas reservoir 4 is measured as a function of time and a first gas property factor Γ*, dependent on a first group of physical properties of the gas or gas mixture, is determined on the basis of the measured values of the pressure drop, with the gas property factor being derived, for example, from a time constant of the pressure drop. Furthermore, a desired physical property or quantity relevant to combustion is determined on the basis of the gas property factor Γ* by aid of correlation.

Advantageously, in the second embodiment of the invention, binary gas mixtures are analysed in regard to their content of the two components forming the gas mixture, since the gas property factor Γ* is intrinsically a continuous function of the gas content x % or (1−x %). With the knowledge of content x % or (1−x %), it is then possible to determine physical properties and/or quantities relevant to combustion of the binary gas mixture from sets of tables or by aid of corresponding calculation programs. Of course, it is also possible to directly correlate these physical properties and/or quantities relevant to combustion of the binary gas mixture with the gas property factor Γ*.

In an embodiment of the method, it is thus possible to determine the percentage of a component contained in a binary gas mixture, in which case the variable to be correlated corresponds either to the percentage of the component in the composition (x %) and/or any other physical property of the binary gas mixture.

Other advantageous embodiments and variants of the method are described in the preceding sections of the specification. The following descriptions provides additional details on the method that may be used if desired.

Advantageously, the inlet valve 3 and the outlet valve 5 are opened first to allow the gas or gas mixture that is to be measured to flow from the main gas duct 1 through the test line 2 and through the measuring apparatus to ensure that no extraneous gas from a previous measurement remains in the measuring apparatus. The inlet valve and outlet valve can be opened via a control unit. In individual cases, the analyzer unit 11, too, can control the inlet valve and the outlet valve, as shown in FIG. 5a. In this case, the outlet valve 5 is closed and the gas reservoir 4, the volume content V of which is known, fills up until the inlet valve 3 is covered. Pressure p and temperature Tin the gas reservoir can be measured with the pressure sensor 8 or the temperature sensor 9, to ensure that the standard volume $V_{norm}$ of the gas or gas mixture contained in the gas reservoir can be deduced at any time.

$$V_{norm} = \frac{p}{1013.25 \text{ mbar}} \cdot \frac{273.15 \text{ K}}{T} \cdot V. \tag{17}$$

If the pressure p in the gas reservoir 4 is higher than the pressure $p_{crit}$, which is required to critically operate nozzle 6, the outlet valve 5 can be opened again. By preference, the pressure p in the gas reservoir exceeds $p_{crit}$ by several bars, so that the pressure drop reading can be performed during this phase of overpressure, while nozzle 6 is always operated critically. Outlet valve 5 now closes again, which concludes the pressure drop measurement. By preference, pressure sensor 8 is installed as a differential pressure sensor relative to outlet 10 of the measuring apparatus. However, it is also possible to provide an additional pressure sensor 8' at the outlet.

During the pressure drop reading, the time-dependent pressure p(t) and the time-dependet temperature T(t) in the pressure reservoir 4 has been measured and recorded by the analyzer unit 11. With these data, the time constant τ in equation (6) or the gas property factor Γ* in equation (6') and the gas property factor Γ* in equation (7) or equation (7') is determined in the analyzer unit.

Depending on the desired quantity relevant to combustion Q, this value is now calculated on the basis of equation (15) with the previously determined correlation function $Q_{corr}=f_{corr}(\Gamma^*)$ in analyzer unit 11.

Figure 5B:
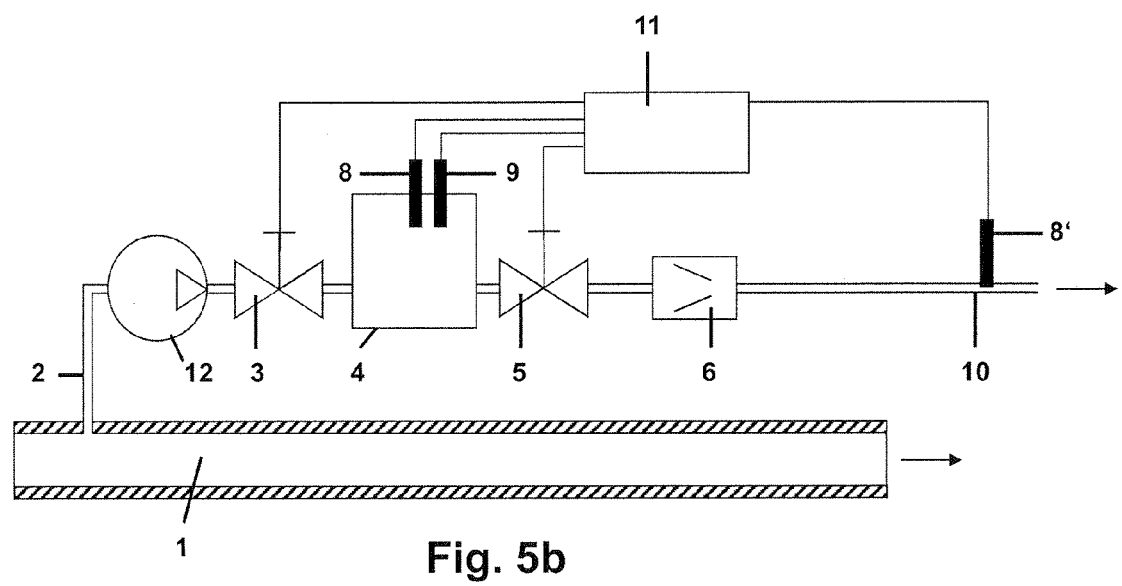
FIG. 5b shows a variant of the exemplary embodiment shown in FIG. 5a, FIG. 6 shows a second exemplary embodiment of a schematic configuration of a measuring apparatus according to a second embodiment of the invention (low pressure variant)

If required, it is possible to provide additionally, as shown in FIG. 5b, a compressor 12', installed, for example, on the inlet side of the gas reservoir 4 to increase the pressure in the gas reservoir.

Figure 6:
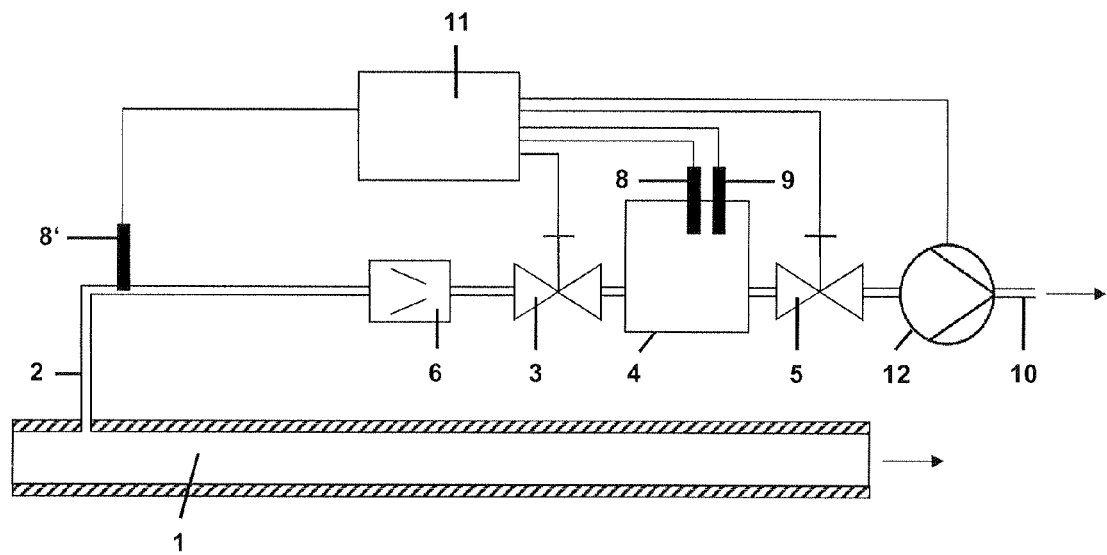

FIG. 6 shows a second exemplary embodiment of the schematic configuration of a measuring apparatus according to the second embodiment of the invention, which is based on low pressure in the gas reservoir. This so-called low pressure variant is advantageous, for example, for the gas supply to end customers. In the second exemplary embodiment, the measuring apparatus, in addition to the gas reservoir 4, comprises a pressure sensor 8, installed on the gas reservoir, an analyzer unit 11, which is configured for carrying out a method according to the second embodiment of the invention, and a critical nozzle 6, in which case the gas reservoir 4 is connected to the critical nozzle 6 for measurement purposes.

If required, the measuring apparatus may comprise one or more of the following additional components: a vacuum pump 12 connected to the gas reservoir 4 to generate low pressure in the gas reservoir, a test line 2 leading to the gas reservoir 4 and which may be connected with a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be located in the test line 2 or main gas duct, and a temperature sensor 9, which is installed in the gas reservoir 4.

Another exemplary embodiment of the method for determining physical properties and/or quantities relevant to combustion of gas and mixtures according to the second embodiment of the invention is described below with reference to FIG. 6. In this exemplary embodiment, the gas or gas mixture flows under pressure through the critical nozzle 6 into the gas reservoir 4. The pressure increase in the gas reservoir 4 is measured as a function of time, and a gas property factor $\Gamma^*$, dependent on a first group of physical properties of the gas or gas mixture, is determined by reference to the measured values of the pressure increase, with the gas property factor being derived, for example, from a proportionality constant of the pressure increase. A desired physical property or quantity relevant to combustion is determined on the basis of the gas property factor $\Gamma^*$ by aid of correlation.

Other advantageous embodiments and variants of the method are described in the preceding sections of the specification. The following description provides additional details on the method that may be used if desired.

In a preceding step, the pressure in gas reservoir 4 is advantageously decreased to such an extent, for example with a vacuum pump 12, that the critical nozzle 6 can be critically operated; in other words, until the pressure in the gas reservoir is less than half the pressure upstream of the critical nozzle. No high vacuum is required. As long as the pressure p and the temperature T can be measured in the gas reservoir 4, it is possible to calculate the gas standard volume that has flown into the gas reservoir. However, it is an advantage, if the pressure is by some factor less than strictly required for critical conditions, because this means that the measurement proceeds during more time accordingly, which makes it possible to determine the proportionality constant more accurately.

For further details on the methods, which may be used if necessary, reference is made to the specification of the first exemplary embodiment, subject to replacement of the term "pressure drop" by the term "pressure increase", where appropriate.

Figure 7:
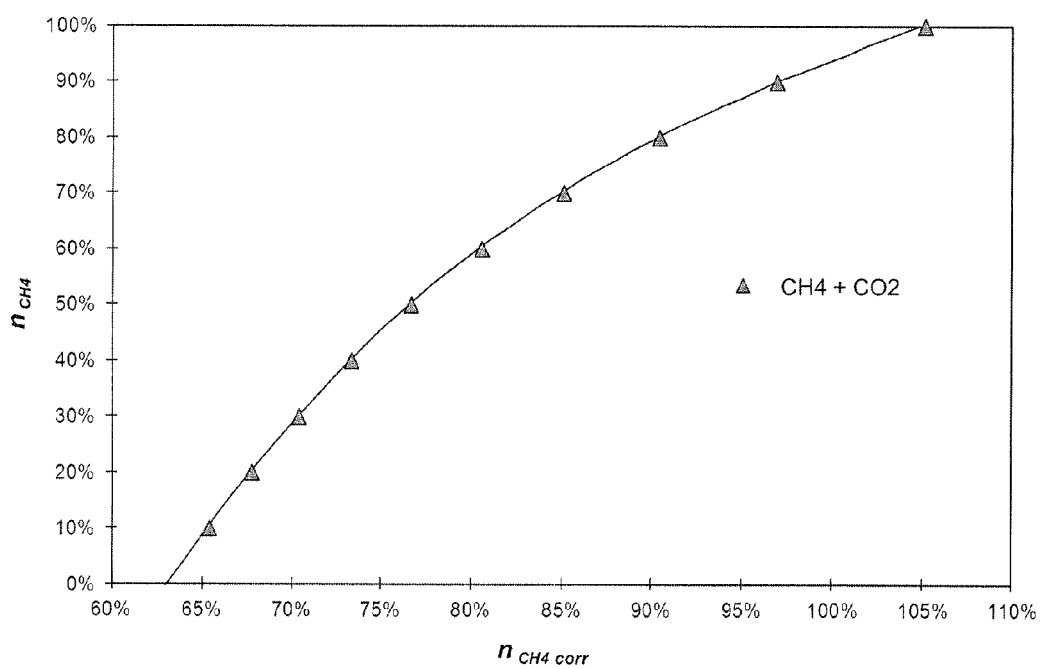
FIG. 7 shows a graphical illustration of the directly measured methane content (ordinate) as a function of the correlated methane content (abscissa) for a binary raw biogas(methane and carbon dioxide).

FIG. 7 illustrates the directly measured methane content $n_{CH4}$ (ordinate) as a function of the correlated methane content $n_{CH4\ corr}$ (abscissa) for a binary raw biogas, composed of methane and carbon dioxide, at standard conditions (0° C., 1013.25 mbar), in which case the correlated methane content was calculated with a method or a measuring apparatus in accordance with the second embodiment of the invention. A typical H-gas was used as a reference gas. The desired variable Q (in this case, the methane content $n_{CH4\ corr}$ in x %) is advantageously determined with the aid of the correlation function $Q_{corr} = a + b \cdot \Gamma^* + c \cdot F + d \cdot \Gamma^{*3}$, in the illustrated example, numerically as a=−7.82, b=22.7, c=−20.4 and d=6.45.

The measuring apparatus described above for determining physical properties and/or quantities relevant to combustion of gas or gas mixtures belongs to a new category, namely "Measurement of the pressure drop or pressure increase in a gas reservoir, wherein the gas flows through a critical nozzle". The components used are inexpensive, which makes it possible to develop new markets, where currently no gas quality sensors are being used for cost reasons. From an accuracy perspective, only a few limitations compared to more expensive, commercially available devices are to be expected, since in this case only one independent measured value, instead of three, is used for the correlation.

In addition, the invention encompasses in a third embodiment the use of a gas reservoir and of a microthermal sensor calibrated for a specific calibration gas or gas mixtures to determine physical properties and/or quantities relevant to combustion of gas or gas mixtures; in this set-up a gas reservoir and a microthermal sensor calibrated for a specific calibration gas or gas mixture for determining physical properties and/or quantities relevant to combustion of gas or gas mixtures are used, with the gas or gas mixture flowing under pressure from the gas reservoir past the microthermal sensor, in which case the volume flow $v_x \cdot A$, determined by the microthermal sensor calibrated for a specific calibration gas or gas mixture, is summed up and compared to the gas volume released from the gas reservoir; from the comparison of the two volumes, a gas property factor $S/v'_x$, dependent on the physical properties of the gas or gas mixture, is determined, in which $v'_x$ represents the flow rate of the released gas volume and in which a desired physical property or quantity relevant to combustion is determined from the gas property factor, which may consist, for example, of $S/v'_x = c_p \cdot \rho / \lambda$ (see equation (9)), through correlation.

The third embodiment of the invention described above can also be seen as a distinct, independent invention.

Figure 8A:
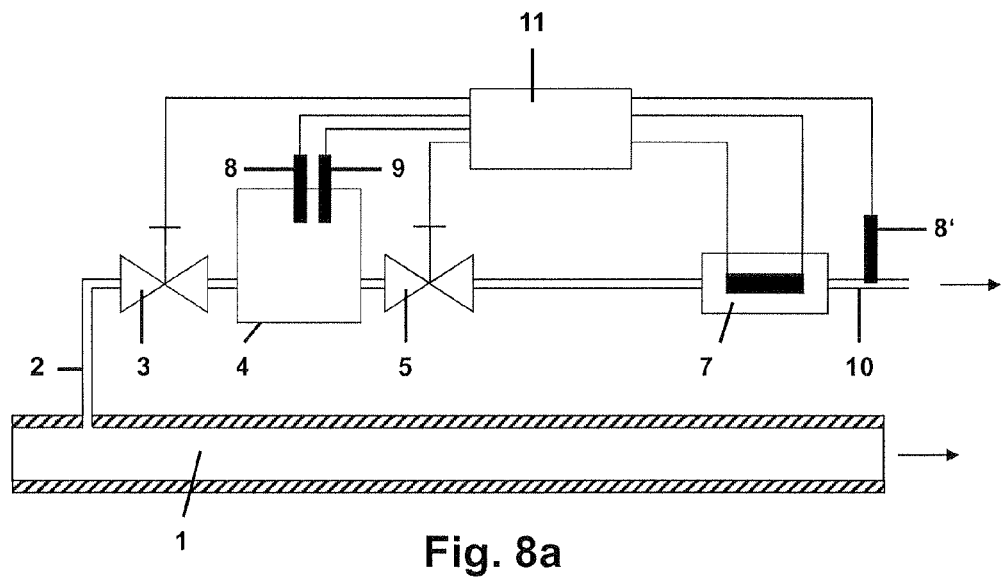
FIG. 8*a* shows an exemplary embodiment of a schematic configuration of a measuring apparatus according to a third embodiment of the invention with a gas reservoir and a microthermal sensor (high-pressure variant)

FIG. 8a shows an exemplary embodiment of the schematic configuration of a measuring apparatus in accordance with the third embodiment of the invention in case the main gas duct 1 is under pressure (high-pressure variant). In the exemplary embodiment, the measuring apparatus consists of an analyzer unit 11, which is configured for carrying out the method in accordance with the third embodiment of the invention, a gas reservoir 4, which is equipped with a pressure sensor 8 and a microthermal sensor 7 to measure the flow and thermal conductivity, in which case the gas reservoir 4 is connected to the microthermal sensor 7 for measurement purposes.

If required, the measuring apparatus may comprise one or more of the following additional components: a test line 2, which leads to the gas reservoir 4, and which may be connected to a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be installed on the outlet 10, a temperature sensor 9, which is installed in the gas reservoir, and a compressor 12', which may be located on the inlet side of the gas reservoir 4 to increase the pressure in the gas reservoir.

An exemplary embodiment of the method for determining physical properties and/or quantities relevant to combustion of gas or gas mixtures in accordance with the third embodiment of the invention is described below with reference to FIG. 8a. In the method, the gas or gas mixture flows under pressure from the gas reservoir 4 past the microthermal sensor 7, calibrated for a specific calibration gas or gas mixture, in which case the volume flow $v_x \cdot A$ is summed up and compared to the gas volume released from the gas reservoir; from the comparison of the two volumes a gas property factor $S/v'_x$, dependent on the physical properties of the gas or gas mixture, is determined, in which $v'_x$ represents the flow rate of the released gas volume, and in which the desired physical property or quantity relevant to combustion is determined from the gas property factor, which may consist, for example, of $S/v'_x = c_p \cdot \rho / \lambda$ (see equation (9)), through correlation.

In an advantageous embodiment of the method, the thermal conductivity $\lambda$ of the gas or gas mixture is determined additionally with the aid of the microthermal sensor 7.

Advantageously, with the third embodiment of the invention, natural gas mixtures are examined as to their classification as H-gases or L-gases (gases with a high (H) or low (L) calorific value), since the gas property factor, which may consist, for example, of $S/v'_x = c_c \cdot \rho / \lambda$ (see equation (9)), corresponds to the reciprocal value of the thermal diffusivity of the gas mixture, with the aid of which—together with the thermal conductivity $\lambda$, which can be measured separately with the microthermal sensor—a distinction between H-gas group and L-gas group can be made.

The classification of a natural gas mixture as belonging to the H-gas or L-gas group can be determined, for example, by identifying the gas property factor ($S/v'_x$) with the reciprocal value of the thermal diffusivity $c_p \cdot \rho / \lambda$, and wherein the classification is made, subject to thermal conductivity, on the basis of a limit value for the thermal diffusivity; above the limit value, a gas mixture is classified as L-gas, and below the limit value, as H-gas.

Thus, in an embodiment variant of the method, the thermal conductivity $\lambda$ of the gas or gas mixture is determined additionally with the aid of the microthermal sensor 7, and a classification of the measured gas as H-gas or L-gas is made in conjunction with the gas property factor $S/v'_x = c_c \cdot \rho / \lambda$.

Other advantageous embodiments and variants of the method are described in the preceding sections of the specification. The following description provides additional details on the method that may be used if desired.

Advantageously, the inlet valve 3 and the outlet valve 5 are opened first to allow the gas or gas mixture that is to be measured flow from the main gas duct 1 through the test line 2 and through the measuring apparatus to ensure that no extraneous gas from a previous measurement remains in the measuring apparatus. The inlet valve and outlet valve can be opened via a control unit. In individual cases, the analyzer unit 11, too, can control the inlet valve and the outlet valve, as shown in FIG. 8a. In this case, the outlet valve 5 is closed and the gas reservoir 4, the volume content V of which is known, fills up until the inlet valve 3 is closed. Pressure p and temperature T in the gas reservoir can be measured with the pressure sensor 8 or the temperature sensor 9, to ensure that the standard volume $V_{norm}$ of the gas or gas mixture contained in the gas reservoir can be deduced at any time.

$$V_{norm} = \frac{p}{1013.25 \text{ mbar}} \cdot \frac{273.15 \text{ K}}{T} \cdot V. \tag{17}$$

The outlet valve 5 can now be opened again. By preference, the pressure p in the gas reservoir 4 is higher than the downstream pressure after the gas reservoir by such a rate that the timespan in which the gas from the gas reservoir 4 flows past the microthermal sensor 7 is long enough to ensure that the volume flow $v_x \cdot A$ can be summed up with sufficient accuracy. Outlet valve 5 now closes again, which concludes the flow measurement. By preference, pressure sensor 8 is installed as a differential pressure sensor opposite outlet 10 of the measuring apparatus. However, it is also possible to provide an additional pressure sensor 8' at the outlet.

Flow data have been measured with the microthermal sensor 7 during the flow measurement and recorded by the analyzer unit 11 to determine factor S in equation (9). Since the inlet valve and the outlet valve close after the flow reading, no gas flows past the microthermal sensor 7 anymore. Now the measurement of the thermal conductivity reading $\lambda$ can take place. The thermal conductivity $\lambda$, recorded in turn by the analyzer unit, is determined with the aid of equation (12).

With these data, the volume flow is summed up in the analyzer unit 11 to form volume $V_{sum}$ and to compare it to the gas volume $V_{diff}$ released from the gas reservoir. Based on the comparison of these two volumes, it is now possible to determine a gas property factor $S/v'_x$, dependent on the physical properties of the gas or gas mixture, in which $v'_x$ represents the flow rate derived from the released gas volume. For practical reasons, the volumes for the comparison are converted to standard conditions for the purposes of the comparison by aid of equation (17), with the result that $v'_x$ consists of $$v'_x = v_x \cdot V_{diff}^{norm} / V_{sum}^{norm} \tag{18}$$

with the released gas volume $v_{diff}^{norm}$ converted to standard conditions and the accumulated volume converted to standard conditions $V_{sum}^{norm}$. Thereafter, depending on the desired quantity Q relevant to combustion, this value is now calculated in the analyzer unit 11 with the aid of equation (15) with the previously determined correlation function $Q_{corr} = f_{corr}(S/v'_x)$ or the value of $S/v'_x$ is being used to classify, in conjunction with the thermal conductivity $\lambda$, a natural gas mixture in the category H-gas or L-gas.

Figure 8B:
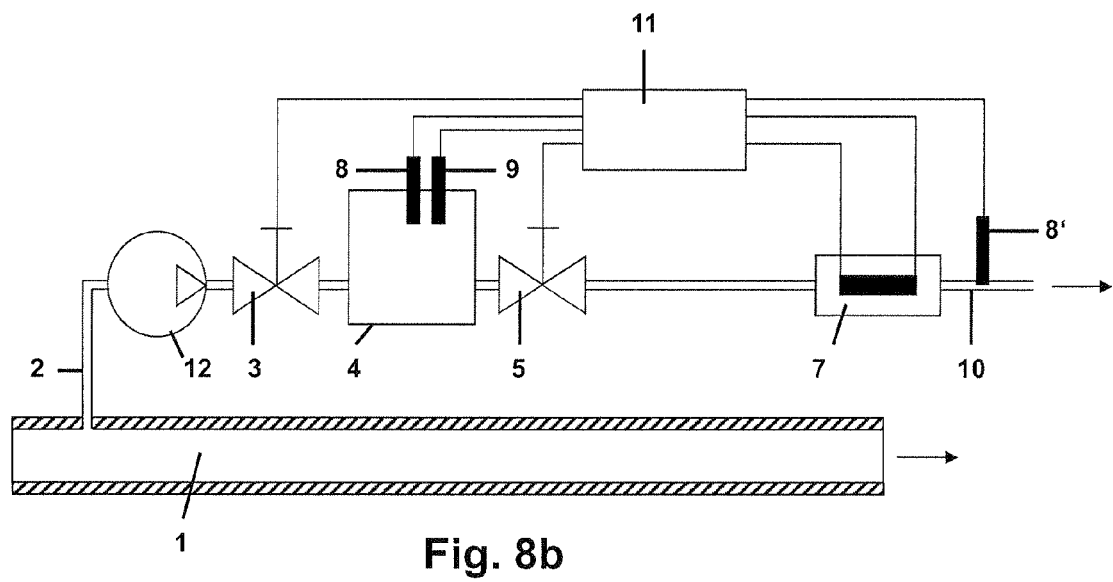
FIG. 8*b* shows a variant of the exemplary embodiment shown in FIG. 8*a*.

If required, it is possible to provide additionally, as shown in FIG. 8b, a compressor 12', installed, for example, on the inlet side of the gas reservoir 4 to increase the pressure in the gas reservoir.

Figure 9:
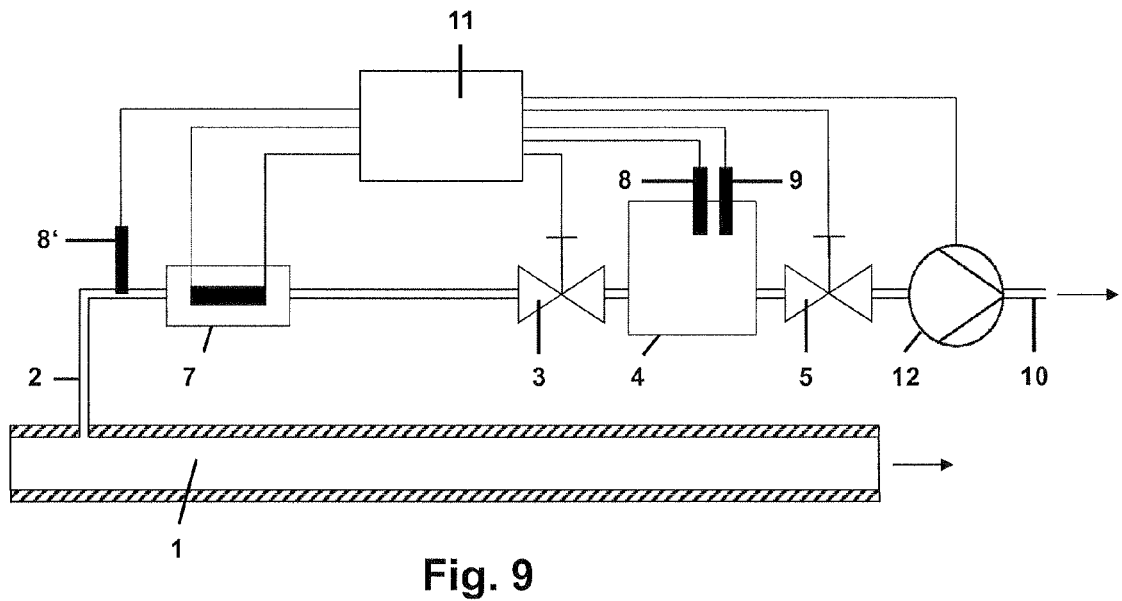
FIG. 9 shows a second exemplary embodiment of a schematic configuration of a measuring apparatus according to a third embodiment of the invention with a gas reservoir and a microthermal sensor (low pressure variant)

FIG. 9 shows a second exemplary embodiment of the schematic configuration of a measuring apparatus according to the third embodiment of the invention, which is based on low pressure in the gas reservoir. This so-called low pressure variant is advantageous, for example, for the gas supply to end customers. In the second exemplary embodiment, the measuring apparatus comprises, in addition to the gas reservoir 4, a pressure sensor 8 on the gas reservoir, an analyzer unit 11, which is configured to carry out a method according to the third embodiment of the invention and a microthermal sensor 7 to measure the flow and the thermal conductivity, in which case the gas reservoir 4 is connected to the microthermal sensor 7 for the purposes of the measurement.

If required, the measuring apparatus may comprise one or more of the following additional components: a vacuum pump 12 connected to the gas reservoir 4 to generate low pressure in the gas reservoir, a test line 2 leading to the gas reservoir 4 and which may be connected with a main gas duct 1 during operation, an inlet valve 3, which may be located in the test line 2 to control the gas supply to the gas reservoir, an outlet valve 5, installed on the outlet side of the gas reservoir to control the flow of gas from the gas reservoir, an outlet 10 for discharging the effluent gas from the measuring apparatus, an additional pressure sensor 8', which may be located in the test line 2 or main gas duct, and a temperature sensor 9, which is installed in the gas reservoir 4.

Another exemplary embodiment of the method for determining physical properties and/or quantities relevant to combustion of gas and mixtures in accordance with the third embodiment of the invention is described below with reference to FIG. 9. In this exemplary embodiment, the gas or gas mixtures flows at a pressure that is typically higher than the downstream pressure after the gas reservoir by such a rate that the timespan in which the gas from the gas reservoir 4 flows past the microthermal sensor 7 is long enough to ensure that the volume flow $v_x \cdot A$ can be summed up with sufficient accuracy. The summed-up volume flow $V_{sum}$ is compared to the gas volume $V_{diff}$ released from the gas reservoir, and from the comparison of the two volumes, a gas property factor $S/v'_x$, dependent on the physical properties of the gas or gas mixture, is determined, in which $v'_x$ represents the flow rate of the released gas volume, and in which the desired physical property or quantity relevant to combustion is determined from the gas property factor, which may consist, for example, of $S/v'_x = c_p \cdot \rho / \lambda$ (see equation (9)), through correlation.

Thus, in an advantageous embodiment of the method, the thermal conductivity $\lambda$ of the gas or gas mixture is determined with the aid the microthermal sensor 7, and a classification of the measured gas as H-gas or L-gas is made, for example, in conjunction with the gas property factor $S/v'_x = c_p \cdot \rho / \lambda$.

For other advantageous embodiments and variants of the method, and for further details on the methods, which may be used if required, reference is made to the preceding sections of the specification, subject to replacement of the term "pressure drop" by the term "pressure increase", where appropriate.

Figure 10:
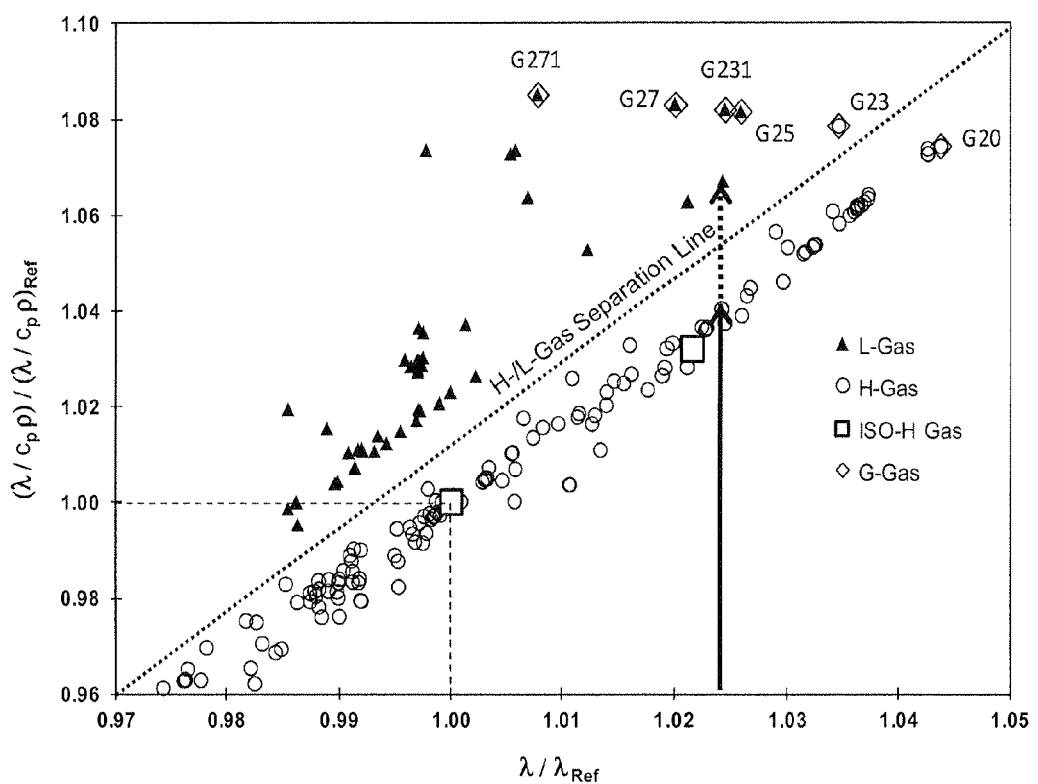
FIG. 10 shows a graphical illustration of the classification of natural gas mixtures by reference to thermal diffusivity (ordinate) with simultaneous knowledge of the thermal conductivity $\lambda$ (abscissa).

FIG. 10 illustrates how a classification as H-gas or L-gas can be made by means of known thermal conductivities $\lambda$ (abscissa) and thermal diffusivities $\lambda/(C_p \rho)$, also referred to as temperature conductivities (ordinate). L-gases above the H/L-gas separation line typically have higher thermal diffusivities than H-gases with the same thermal conductivity below the separation line (double arrow at $x \approx 1.024$). Since the gas property factor $S/v'_x = c_p \cdot \rho / \lambda$ is essentially equivalent to the reciprocal value of the thermal diffusivity of the gas mixture, it is thus possible to make the distinction between H-gas and L-gas with the aid of the additionally measured thermal conductivity $\lambda$. All values are shown at standard conditions (0° C., 1013.25 mbar). A typical H-gas was used as reference gas (dashed line for the coordinate (1.00, 1.00)).

The measuring apparatus described above for determining physical properties and/or quantities relevant to combustion of gas or gas mixtures belongs to a new category, namely "Thermal conductivity and flow measurement with the aid of a microthermal sensor, cumulative adding of the flow values and a comparison of the released volume from a reference volume. Thereafter, classification of natural gases as H-gas or L-gas". The components used are inexpensive, which makes it possible to develop new markets, where currently no gas quality sensors are being used for cost reasons. From an accuracy perspective, only a few limitations compared to more expensive, commercially available devices are to be expected, since this apparatus uses only two instead of three independent measured variables for the correlation.

The invention claimed is:

1. A method for determining physical properties and/or quantities relevant to combustion of a gas and/or a gas mixture, the method comprising:
    flowing the gas and/or gas mixture from a gas reservoir through a critical nozzle and past a microthermal sensor, wherein the same mass flow is applied to the critical nozzle and the microthermal sensor;
    measuring a pressure drop in the gas reservoir as a function of time;
    determining a first gas property factor ($\Gamma^*$), which is dependent on a first group of physical properties of the gas and/or gas mixture, wherein the first gas property is derived based on a time constant of the pressure drop;
    determining a second gas property factor ($\Gamma$), which is dependent on a second group of physical properties of the gas and/or gas mixture, from a flow signal generated by the microthermal sensor, wherein the second gas property factor contains or is dependent on a heat capacity ($c_p$) of the gas and/or gas mixture;
    determining a thermal conductivity ($\lambda$) of the gas and/or gas mixture using the microthermal sensor; and
    determining a physical property and/or a quantity relevant to combustion through a correlation between the physical property and/or the quantity relevant to combustion, and the first and second gas property factors ($\Gamma^*$, $\Gamma$) and the thermal conductivity ($\lambda$).

2. The method according to claim 1, in which a starting point of the determination of the first gas property factor is an exponential decline of pressure in the gas reservoir and/or the first gas property factor is formed in addition by measuring a temperature (T) of the gas and by omitting all gas-unrelated variables.

3. The method according to claim 1, in which the second gas property factor ($\Gamma$) contains a quotient of the heat capacity ($c_p$) divided by thermal conductivity ($\lambda$) of the gas or gas mixture, or is dependent on the same, and/or in which the second gas property factor is formed by measuring the temperature (T) additionally and by omitting all gas-unrelated variables.

4. The method according to claim 1, wherein the first and the second gas property factors ($\Gamma^*$, $\Gamma$) are validated by comparing the values for the total volume of released gas or gas mixture by:
    measuring the pressure and temperature in the gas reservoir at a start and an end of measurement of the pressure drop and by determining a released standard volume by reference to a known volume of the gas reservoir;
    summing a standard flow measured with the microthermal sensor during a time interval between the start and end of measurement of the pressure drop to determine a summed standard volume;
    comparing the released standard volume to the summed standard volume; and
    in case of a discrepancy between the released standard volume and the summed standard volume, adjusting the first and/or the second gas property factor ($\Gamma^*$, $\Gamma$).

5. A method for determining physical properties and/or quantities relevant to combustion of gas or gas mixtures, the method comprising:
    flowing the gas or gas mixture under pressure through a critical nozzle and past a microthermal sensor into a gas reservoir, with the same mass flow being applied to the critical nozzle and the microthermal sensor;

measuring a pressure increase in the gas reservoir as a function of time to obtain measured values of the pressure increase;

determining a first gas property factor ($\Gamma^*$) dependent on a first group of physical properties of the gas or gas mixture, on the basis of the measured values of the pressure increase;

determining a second gas property factor ($\Gamma$), which is dependent on a second group of physical properties of the gas or gas mixture, from a flow signal of the microthermal sensor, with the second gas property factor containing or depending on a heat capacity ($c_p$) of the gas or gas mixture;

determining a thermal conductivity ($\lambda$) of the gas or gas mixture using the microthermal sensor; and determining a physical property or a quantity relevant to combustion using a correlation between the physical property or the quantity relevant to combustion, and the first and second gas property factors ($\Gamma^*$, $\Gamma$) and the thermal conductivity ($\lambda$).

6. The method according to claim 5, in which a starting point of the determination of the first gas property factor is a linear increase of the pressure increase, and the first gas property factor ($\Gamma^*$) is derived from a proportionality constant of the pressure increase, and/or in which the first gas property factor is formed in addition by measuring a temperature (T) of the gas or gas mixture and a nozzle inlet pressure, and by omitting all gas-unrelated variables.

7. The method according to claim 5, in which the second gas property factor ($\Gamma$) contains or is dependent on a quotient of heat capacity ($c_p$) divided by thermal conductivity ($\lambda$) of the gas or gas mixture, and/or in which the second gas property factor is formed in addition by measuring a temperature (T) of the gas or gas mixture and by omitting all gas-unrelated variables.

8. The method according to claim 5, where the gas property factors ($\Gamma^*,\Gamma$) are validated by comparing values for volumes of the gas or gas mixture fed into the gas reservoir by:

measuring a pressure and a temperature in the gas reservoir at a start and an end of the measured pressure increase and by determining a released standard volume fed into the gas reservoir by reference to a known volume of the gas reservoir;

summing a standard flow of the gas or gas mixture as measured with the microthermal sensor during a time interval between the start and the end of the measured pressure increase to determine a summed standard volume;

comparing the released standard volume fed into the gas reservoir to the summed standard volume and based on the comparison determining if a discrepancy exists; and in response to the determination of a discrepancy, adjusting the first and/or the second gas property factor.

9. The method according to claim 1, wherein the method includes calibrating the flow signal of the microthermal sensor, by:

calibrating the flow signal of the microthermal sensor for a specific calibration gas or gas mixture;

determining a ratio ($\Gamma/\Gamma^*$) of the second gas property factor to the first gas property factor for an unknown gas or gas mixture, with the second gas property factor being determined from the flow signal of the microthermal sensor;

measuring a pressure and a temperature in the gas reservoir at a start and an end of the measured pressure increase and by determining a released standard volume fed into the gas reservoir by reference to a known volume of the gas reservoir;

summing a standard flow of the gas or gas mixture as measured with the microthermal sensor during a time interval between the start and the end of the measured pressure increase to determine a summed standard volume; and comparing the released standard volume and the summed standard volume and using the comparison to adjust a ratio of the second gas property factor to the first, and to adapt the second gas property factor ($\Gamma$).

10. The method according to claim 1 where the physical property is a density or the thermal conductivity or the heat capacity or the viscosity of the gas or gas mixture, and/or where the quantity relevant to combustion is the energy content or the calorific value or the Wobbe index or the methane number or the air requirement of the gas or gas mixture.

11. The method according to claim 1, where the correlation of the physical property or the quantity relevant to combustion (Q) is determined using a correlation function:

$$Q=f_{corr}(\Gamma\Gamma^*,\lambda)=\text{const}\cdot\Gamma^r\cdot\Gamma^{*s}\cdot\lambda^t,$$

wherein r, s and t are exponents, and const is a constant.

12. The method according to claim 1, where the pressure in the gas reservoir is higher at the start of the measured pressure drop than a critical pressure of the critical nozzle, and an external pressure of the gas or gas mixture downstream of the critical nozzle is less than half of the critical pressure, or where a pressure in the gas reservoir at the start of the measured pressure increase is less than half of the critical pressure of the critical nozzle, and the pressure upstream of the critical nozzle is higher than the critical pressure.

13. A measuring apparatus for determining a physical property and/or a quantity relevant to combustion of gas and/or gas mixtures comprising:

an analyzer unit configured to carry out a procedure in accordance with claim 1 or 5, a gas reservoir equipped with a pressure sensor, a critical nozzle, and a microthermal sensor to measure the flow and thermal conductivity, with the gas reservoir being connected to the critical nozzle and the microthermal sensor for measurement purposes.

14. A method to use a gas reservoir and a critical nozzle for determining physical properties and/or quantities relevant to combustion of gas or gas mixtures, the method comprises:

flowing the gas or gas mixture under pressure from the gas reservoir through the critical nozzle;

measuring a pressure drop in the gas reservoir as a function of time;

determining a gas property factor ($\Gamma^*$), dependent on physical properties of the gas or the gas mixture, from the measured values of the pressure drop, wherein the gas property factor ($\Gamma^*$) is derived using a time constant of the measured pressure drop; and determining a physical property or a quantity relevant to combustion through a correlation between the physical property or the quantity relevant to combustion and the gas property factor ($\Gamma^*$).

15. A method to determine a physical property and/or a quantity relevant to combustion of a gas or a gas mixture using a gas reservoir and a microthermal sensor, calibrated for a specific calibration gas or gas mixture, the method comprises:
- flowing the gas or gas mixture under pressure from the gas reservoirpast the microthermal sensor;
- determining a flow rate ($v_x$) of the gas or gas mixture using the microthermal sensor;
- determining a summed-up volume flow ($v_x \cdot A$) based on the flow rate ($v_x$) over a period of time;
- comparing the summed up volume flow to a gas volume released from the gas reservoir;
- determining a gas property factor ($S/v'_x$), dependent on physical properties of the gas or gas mixture, from the comparison, wherein the quantity ($v'_x$) represents a flow rate determined from the released gas volume, and wherein the gas property factor comprises the heat capacity ($c_p$) of the gas or gas mixture or is dependent on the same; and
- determining a physical property or a quantity relevant to combustion on the basis of the gas property factor through a correlation between the physical property or the quantity relevant to combustion and the gas property factor.

16. A method to determine a physical property of a gas comprising:
- flowing a gas from a reservoir through a critical nozzle and a microthermal sensor wherein the mass flow of the gas through the critical nozzle is the same mass flow through the microthermal sensor;
- measuring a pressure drop in the reservoir as the gas flows through the critical nozzle;
- determining a first gas property factor based on the measured pressure drop;
- determining a second gas property factor based on a flow signal generated by the microthermal sensor;
- determining a thermal conductivity of the gas using the microthermal sensor, and
- determining a physical property of the gas based on a correlation from the thermal conductivity and at least one of the first and second gas property factors.

* * * * *

UNITED STATES PATENT AND TRADEMARK OFFICE
CERTIFICATE OF CORRECTION

PATENT NO. : 9,612,229 B2
APPLICATION NO. : 14/282562
DATED : April 4, 2017
INVENTOR(S) : Philippe Pretre et al.

Page 1 of 1

It is certified that error appears in the above-identified patent and that said Letters Patent is hereby corrected as shown below:

On the Title Page

Item [57], Line 2, change "including: flowing a gas a critical nozzle" to --including: flowing a gas through a critical nozzle--

In the Specification

Column 6, Line 35, change "(15)" to --(16)--

Column 12, Line 27, change "temperature Tin" to --temperature $T$ in--

Column 16, Line 22, change "temperature Tin" to --temperature $T$ in--

Column 19, Line 58, change "temperature Tin" to --temperature $T$ in--

Column 18, Line 1, change "$Q_{corr} = a+b \cdot \Gamma^* +c \cdot F+d \cdot \Gamma^{*3}$" to --$Q_{corr} = a+b \cdot \Gamma^* +c \cdot \Gamma^{*2}+d \cdot \Gamma^{*3}$--

In the Claims

Claim 11, Column 24, Line 26, change "$Q = f_{corr}(\Gamma\Gamma^*, \lambda) = const \cdot \Gamma^r \cdot \Gamma^{*s} \cdot \lambda^t$" to --$Q = f_{corr}(\Gamma, \Gamma^*, \lambda) = const \cdot \Gamma^r \cdot \Gamma^{*s} \cdot \lambda^t$--

Signed and Sealed this
Sixth Day of February, 2018

Joseph Matal
*Performing the Functions and Duties of the*
*Under Secretary of Commerce for Intellectual Property and*
*Director of the United States Patent and Trademark Office*